(12) United States Patent
Hartman

(10) Patent No.: US 12,740,833 B2
(45) Date of Patent: Sep. 22, 2026

(54) PATIENT SPECIFIC DYNAMIC NAVIGATION TRACKER ARM MOUNT APPARATUS AND METHOD

(71) Applicant: Michael J Hartman, Lewisberry, PA (US)

(72) Inventor: Michael J Hartman, Lewisberry, PA (US)

(73) Assignee: Digital Provisionalization Technologies, Inc., Lewisberry, PA (US)

( * ) Notice: Subject to any disclaimer, the term of this patent is extended or adjusted under 35 U.S.C. 154(b) by 0 days.

(21) Appl. No.: 17/449,842

(22) Filed: Oct. 4, 2021

(65) Prior Publication Data

US 2022/0104885 A1 Apr. 7, 2022

Related U.S. Application Data

(60) Provisional application No. 63/087,954, filed on Oct. 6, 2020.

(51) Int. Cl.
*A61B 34/20* (2016.01)
*A61B 1/24* (2006.01)
(Continued)

(52) U.S. Cl.
CPC ................ *A61B 34/20* (2016.02); *A61B 1/24* (2013.01); *A61C 13/0004* (2013.01);
(Continued)

(58) Field of Classification Search
CPC ........... A61C 1/082; A61C 1/084; A61C 8/00; A61C 8/0089; A61C 8/009; A61B 17/1673; A61B 34/00–77
(Continued)

(56) References Cited

U.S. PATENT DOCUMENTS 8,167,617 B2 5/2012 Saliger et al.
8,938,282 B2 * 1/2015 Daon ...................... A61B 1/24 600/407

(Continued)

FOREIGN PATENT DOCUMENTS

WO WO-2016101368 A1 * 6/2016 ............... A61C 1/08
WO WO-2025189285 A1 * 9/2025 ............. A61B 90/39

OTHER PUBLICATIONS

Englisht Translation of WIPO Patent Application No. WO2016101368 (2016) (Year: 2016).*

(Continued)

*Primary Examiner* — Matthew M Nelson
(74) *Attorney, Agent, or Firm* — Spilman, Thomas & Battle, PLLC; Shane P. Riley; William P. Smith

(57) ABSTRACT

A system and method for a tracker arm mount for dynamic navigation is provided. The tracker arm mount accurately adapts to the patient's jawbone and is temporarily secured to the bone with screws engaging the full thickness of the bone. The tracker arm supports an occlusal positioning device and a dental prosthesis. The tracker arm mount is based off digital imaging records. The inner surface is fabricated to closely contour the outer surface, or buccal, contour of the patient's jaw bone. Attachment apertures avoid vital structures and may accept reinforcement collars. Fasteners are placed through the attachment apertures to fixate the mount to the patient's jaw bone. Slots accept corresponding tabs from an occlusal positioning device, interim dental prosthesis, or other device.

12 Claims, 7 Drawing Sheets

(51) Int. Cl.
*A61C 13/00* (2006.01)
*A61B 17/16* (2006.01)

(52) U.S. Cl.
CPC ... *A61B 17/1673* (2013.01); *A61B 2034/2057* (2016.02); *A61B 2034/2072* (2016.02)

(58) Field of Classification Search
USPC ........................................................... 433/29
See application file for complete search history.

(56) References Cited

U.S. PATENT DOCUMENTS

| | | | | |
|---|---|---|---|---|
| 9,402,691 | B2 | 8/2016 | Merritt et al. | |
| 9,782,238 | B2 | 10/2017 | Kopelman | |
| 9,795,458 | B2 | 10/2017 | Llop | |
| 9,844,324 | B2 | 12/2017 | Merritt et al. | |
| 9,943,374 | B2 | 4/2018 | Merritt et al. | |
| 9,949,807 | B2 | 4/2018 | Orth et al. | |
| 10,188,486 | B2 | 1/2019 | Schneider | |
| 10,278,789 | B2 | 5/2019 | Llop | |
| 10,307,226 | B2 | 6/2019 | Llop | |
| 10,350,008 | B2 | 7/2019 | Gibbs et al. | |
| 10,398,530 | B2 | 9/2019 | Llop | |
| 10,405,945 | B2 | 9/2019 | Llop | |
| 10,517,694 | B2 | 12/2019 | Llop | |
| 10,543,064 | B2 | 1/2020 | Kuo | |
| 10,639,129 | B2 | 5/2020 | Llop | |
| 10,639,204 | B2 | 5/2020 | Cheung et al. | |
| 10,675,130 | B2 | 6/2020 | Kopelman | |
| 2008/0085489 | A1 | 4/2008 | Schmitt | |
| 2012/0316486 | A1* | 12/2012 | Cheung | G01S 17/06 342/450 |
| 2016/0074129 | A1* | 3/2016 | Merritt | A61B 34/20 433/29 |
| 2017/0112592 | A1* | 4/2017 | Groscurth | A61C 1/084 |
| 2017/0265963 | A1* | 9/2017 | Yau | A61C 1/084 |
| 2017/0348055 | A1* | 12/2017 | Salcedo | A61C 1/084 |
| 2018/0333229 | A1* | 11/2018 | Watson | A61C 8/0053 |
| 2019/0223988 | A1* | 7/2019 | Palmer | A61B 6/032 |
| 2024/0206983 | A1* | 6/2024 | Guthart | A61B 34/20 |

OTHER PUBLICATIONS

Dynamic Navigation for Dental Implant Surgery, Neeraj Panchal et al., Elsevier Inc. (2019) (Year: 2019).*

* cited by examiner

PATIENT SPECIFIC DYNAMIC NAVIGATION TRACKER ARM MOUNT APPARATUS AND METHOD

CROSS-REFERENCE TO RELATED APPLICATIONS

This patent application claims the benefit of U.S. Provisional Patent Application Ser. No. 63/087,954 filed Oct. 6, 2020, entitled "Patient Specific Dynamic Navigation Tracker Arm Mount Apparatus and Method", which patent application is hereby incorporated by reference.

BACKGROUND

The present invention generally relates to dynamic navigation use in the oral and maxillofacial region. More particularly how the tracker arm can be fixated to the patient and combined with a foundation guide during a full arch dental implant rehabilitation surgery.

Dynamic navigation is a form of surgical guidance that allows the surgeon to visualize on a computer monitor a probe or instrument in relation to a patient's computed tomography (CT) scan. It can be generally thought of as a global positioning system (GPS) whereas the "car" is the surgical instrument and the overlying "map" is a previously acquired CT scan of the patient. It can be used during surgery to aid in detection of anatomical structures such as tumors or fractured bones. It is currently used in the fields of neurosurgery, orthopedic surgery, oral and maxillofacial surgery, and dentistry. In dentistry, there is a FDA approved dynamic navigation device to aid in the site development and placement of dental implants. For simplicity, dental implants can be compared to replacement tooth roots made of titanium that once integrated into bone can accept a corresponding crown. Multiple implants in the same jaw can be used to attach a complete set of teeth referred to in dentistry as a hybrid prosthesis. This hybrid prosthesis can be fabricated to resemble missing teeth and surrounding gum tissue. The generalized term for a procedure where the remaining teeth are removed, the jaw bone is leveled, multiple dental implants are placed in the jaw bone, and a corresponding hybrid prosthesis is attached to the dental implants is called a full arch dental implant rehabilitation.

The dynamic navigation currently used to aid in the placement of dental implants as well as it's associated dental implant treatment planning software has been reported in peer reviewed journals to be precise and accurate. The use of this device in dental implant surgery decreases the risks of surgical complications such as damage to adjacent tooth roots, nerves, and blood vessels.

The description of how dynamic navigation in implant dentistry works is as follows. A patient's three-dimensional X-ray (cone beam computed tomography (CBCT)) is loaded into the dynamic navigation software. A treatment plan is created by placing virtual dental implants onto the uploaded CBCT scan. At the time of surgery, an optical array, or tracker, is attached to a surgical instrument or probe. A second tracker is affixed, or seated, onto the patient's teeth. This occurs by warming and then molding a clip composed of a thermoplastic material unto the patient's teeth. When set, this provides the proper consistency to safely remove without damaging the teeth but yet re-insert in a secure, accurate, position. This clip is used as the mount for the tracker. These trackers are secured onto the mount and are detected by overhead stereotactic cameras which detect the position of the surgical instrument in relation to the patient and relay the information back to a computer monitor where the position is seen in real time over the patient's CBCT scan. The surgeon essentially "follows the map" to place the dental implant into its planned position.

Occasionally, a tracker arm mount cannot be solely secured onto the patient's teeth. Currently available options include screws or plates which can be secured into the patient jaw bone to attach a tracker arm.

Placing dental implants in a precise and accurate position is only one part of a successful patient case or outcome. The dental implants must still be planned in a manner to ensure that the ultimate restorative outcome (i.e. the patient's new teeth) will be esthetically pleasing and hygienically easy to clean for the patient. This requires the upper and lower teeth occlude, or intersect, correctly and that there is enough space created by reducing the patient's jaw bone to accommodate the associated implant parts and new teeth.

Increasingly, patient's that do not have teeth or one's requiring the removal of their remaining teeth want a solution where one surgery can be performed to place dental implants and attach corresponding temporary teeth. One may be familiar with the so called teeth in a day procedure.

Several teeth in a day solutions are available to dental surgeons. In general the steps and components are listed below: 1) removal of the remaining teeth and placing a guide which functions to level and remove the appropriate amount of jaw bone; 2) placement of a dental implant surgical guide to aid in the accurate placement of the dental implants; 3) placement of the dental implants; 4) attachment of fixtures to the top of the dental implants; 5) a pick-up of the temporary teeth whereby the prosthesis is aligned over the fixtures of the dental implants and secured to it; and 6) verification the teeth are in correct position and are occluding properly.

The above-mentioned process has greatly improved the overall patient experience in these teeth in a day procedures. Specifically, the procedure saves overall time and generally provides a product that is more esthetic and hygienic than previous described techniques and methods.

What is needed is a system and/or method that satisfies one or more of these needs or provides other advantageous features. Other features and advantages will be made apparent from the present specification. The teachings disclosed extend to those embodiments that fall within the scope of the claims, regardless of whether they accomplish one or more of the aforementioned needs.

SUMMARY

One embodiment relates to a dynamic navigation method for oral and maxillofacial surgery using a tracker arm, includes acquiring digital data associated with a patient; generating a dental surgery treatment plan; placing a plurality of virtual dental implants: designing a tracker arm, a tracker arm mount and a foundation guide based on the surgery treatment plan; designing a prosthesis and a positioning device for attaching the tracker arm mount to a jawbone of the patient; fabricating the prosthesis and the tracker arm mount positioning device; performing a reflection of a gum tissue of the patient: attaching the tracker arm mount; attaching the tracker arm mount positioning device onto the teeth accurately repositioning the tracker arm mount with the positioning device; and attaching an optical tracking device to the tracker arm mount.

Another embodiment relates to a dynamic navigation system for oral and maxillofacial surgery. The system includes a tracker arm, a tracker arm mount and a foundation guide. The tracker arm mount includes a threaded portion attached by a connecting arm to a body. The body has a top surface and an inner surface corresponding with an outer surface contour of a jaw bone. Receiving slots are included on the body. Apertures are provided to receive a fastener for attachment of the tracker arm mount to the jawbone.

Another embodiment relates to a dynamic navigation system for oral and maxillofacial surgery has a tracker arm and a tracker arm mount. The tracker arm mount includes a threaded portion for receiving an optical tracking device. The tracker arm mount includes at least one aperture for receiving a fastener for attachment to a jawbone.

The tracker arm mount accurately adapts to the patient's boney anatomy. The mount is temporarily secured to the bone with screws engaging the full thickness of the bone.

Advantage of the tracker arm mount include patient specific configurations. CAD/CAM software is used to format the patients computed tomography (CBCT) in a format that allows the mount to be contoured to the jaw bone for an accurate and snug fit.

The tracker arm mount may be designed to avoid vital structures and include predetermined implant positions.

Another advantage is a threaded portion for attaching an optical tracking device. The tracker arm may be adapted for various other methods of optical tracker attachment per dynamic navigation specifications.

Still other advantages include low profile mount design; steel guide tubes for the areas of screw insertion to prevent mount material from being imbedded into jaw bone; and anchor points to receive other patient specific designed and fabricated attachments.

The top of the mount may include a flat edge which may be used as a reference for jaw bone reduction.

The tracker arm mount may be produced from additive or subtractive methods of fabrication, e.g., three-dimensional printing or laboratory milling machine.

The tracker arm mount can have an associated tracker arm mount positioning device. This device is designed to seat on top of the teeth. The positioning device and tracker arm mount arm attached and seated as one unit. The tracker arm mount is fixated with screws. Once secured, the positioning device is removed.

The temporary prosthesis may be designed with corresponding struts to be secured into the tracker arm mount.

Placement of the tracker arm in surgeries where teeth cannot be used as a mount is technically challenging even for experienced users of dynamic navigation. These challenges are listed below and be broken into two main categories: attachment-related and location related.

Attachment options are disclosed, including a pair of screws which can be inserted into the jaw bone to accept the tracker arm attachment and a stainless steel plate which can be fixated onto the jaw which can accept the tracker arm. Through personal experience, the length of the screws is typically not long enough to securely anchor the tracker arm mount during the dynamic navigation procedure and can lead to dislodgement of the tracker arm.

If the tracker arm mount becomes dislodged, it must be resecured and the dynamic navigation device must be recalibrated to ensure accuracy. Calibration relies on anatomical landmarks from the patient's CBCT. If these landmarks have been removed or modified during the procedure during teeth extractions or bone leveling, it may make recalibration very difficult or impossible. This may cause the procedure to be terminated or force the surgeon to place the implants in a freehand method whereby he or she relies on surrounding anatomy to place the dental implants. This freehand method may increase the risk of potential complications such as incorrect implant placement or damage to surrounding vital structures.

The use of the stainless steel plate is another option to rigidly secure the tracker arm to the patient's jaw bone. However, it's size requires a large footprint over the jaw bone. The plate is flat and is constructed of a material that prevents it's easy manipulation to be bent to loosely correspond to the patients unique contours of the jaw. Due to its large footprint in relation to the jaw bone, additional soft tissue reflection is required to secure the plate. This can lead to additional post-operative pain and swelling to the patient. The large footprint may also interfere with the planned sites for dental implant placement.

Regardless of the attachment option used, the surgeon must be aware of several factors when deciding where to affix the tracker arm mount. In general, the attachments must be affixed into solid bone to avoid dislodgement. Currently, the screws available for attachment are of a length that may not be long enough to provide secure attachment into the bone.

Certain anatomical structures may limit positioning. In the lower jaw (mandible) a nerve that provides sensation to the lip and teeth runs through the posterior aspect. The surgeon must rely on pre-operative imaging and experience as to not damage the nerve while affixing either mount. In the upper jaw (maxilla) the posterior portion is composed of the maxillary sinus, affixing the mount in this area may lead to post-operative complications such as sinus infection or a communication created from the sinus into the oral cavity.

The surgeon must also plan the placement of the tracker arm mount so as to not interfere with the placement of the dental implants. The screws used to affix the mount must not be in the planned path of the dental implant placement. In cases where multiple implants are planned, this can lead to a limited space for the mounting screws to be placed.

Dynamic navigation relies on a clear field of view light emittance form the source to the instrument and tracker arrays. Disruption of this field of view causes loss of instrument location on the dynamic navigation monitor. It is essential the tracker arm be designed in a way, per surgeon preference, to provide a location for the patient array to be in position which will not have a prohibitive field of view from the overhead stereotactic camera. Factors which may contribute to surgeon preference include their operating handedness, either right or left-handed, and their preferred location on of the dynamic navigation monitor, i.e. at the head or feet of the patient. Current options for tracker arms come in predetermined lengths and configurations. Per experience, the current commercially available options provide a less than ideal position for the patient tracker array to be secured and provide a clear field of view for stereotactic camera detection.

One application of dynamic navigation implant surgery may be in a teeth in a day type procedure. Currently, these procedures are accomplished with the use of a static guide which aids the surgeon in site development and placement of dental implants. These sites have been planned prior to surgery and corresponding temporary teeth have been fabricated. Dynamic navigation use should be considered in these types of procedures.

Dynamic navigation use has several advantages over static guides for the use of guided dental implant surgery. The use of dynamic navigation is less cumbersome than using a static guide and does not require additional dental implant components. Normal length drills are used with dynamic navigation as opposed to static guides which require longer drills to overcome the additional distance needed to compensate for the thickness of static guides. These longer drills can be very difficult to use in instances where there is limited space due to the patient's anatomy or limited mouth opening. In some instances, the static guide may not accurately fit over the patient's teeth or jaw bone. If the static guide does not fit as planned, the entire teeth in a day procedure will be inaccurate and may have to be aborted.

Another advantage to dynamic navigation is the surgeon has the ability to see the jaw bone during implant site development and placement. Static guides obscure the view of the bone and the surgeon can only assess the surrounding bone once the implants have been placed and the guide has been removed. In some instances, dental implant placement may not be satisfactory due to surrounding bony architecture and may require removal and placement in a different site.

The present invention aims to eliminate the above listed disadvantages by designing a patient specific tracker arm and mount for dynamic navigation cases where a patient's dentition cannot be used as the foundation for the mount. In instances where a moldable plastic clip over the patient's teeth cannot be used as a tracker mount, a patient specific mount is designed to seat onto the teeth as well as surrounding soft tissue and has a corresponding guide tube to allow a fixation screw into the underlying jaw bone for additional fixation. This patient tracker arm mount is designed in way that will allow attachment into solid bone with appropriate length screws to engage an adequate amount of jaw bone. It is designed "around" the proposed dental implant sites so as not to interfere with dental implant placement. It is also designed to avoid vital structures in the jaws so to reduce potential surgical complications such as nerve damage or sinus infection. In cases where vertical bone reduction is required or where a teeth in a day procedure is planned, the tracker arm mount is designed in a manner that also acts as a guide for bone removal and have struts to accurately position the planned temporary teeth (prosthesis).

Alternative exemplary embodiments relate to other features and combinations of features as may be generally recited in the claims.

BRIEF DESCRIPTION OF THE FIGURES

The application will become more fully understood from the following detailed description, taken in conjunction with the accompanying figures, wherein like reference numerals refer to like elements, in which.

DETAILED DESCRIPTION OF THE EXEMPLARY EMBODIMENTS

Before turning to the figures which illustrate the exemplary embodiments in detail, it should be understood that the application is not limited to the details or methodology set forth in the following description or illustrated in the figures. It should also be understood that the phraseology and terminology employed herein is for the purpose of description only and should not be regarded as limiting.

The present invention provides a patient specific solution to tracker arm mounting for dynamic navigation surgery. This invention could be used in any dynamic navigation surgical system requiring a patient tracker arm to be fixated into surrounding hard tissue.

In regard to dental implant surgery, the patient specific tracker arm can be planned in manner to be secure, avoid vital structures, and avoid planned dental implant placement locations. It can also be incorporated into a more complex foundation guide to offer a teeth in a day dental implant full arch oral rehabilitation solution possibly consisting of a tracker arm mount/bone foundation guide with corresponding temporary teeth which can be stacked or attached to said guide for accurate placement of the teeth to be picked up or secured onto the corresponding dental implant attachments.

Referring to FIGS. 1-11, The present invention 10 discloses a tracker arm mount that can accommodate and support an occlusal positioning device 20 and subsequent interim dental prosthesis 30. The tracker arm mount 10 is designed based on digital imaging records from the patient (not shown.)

Figure 1:
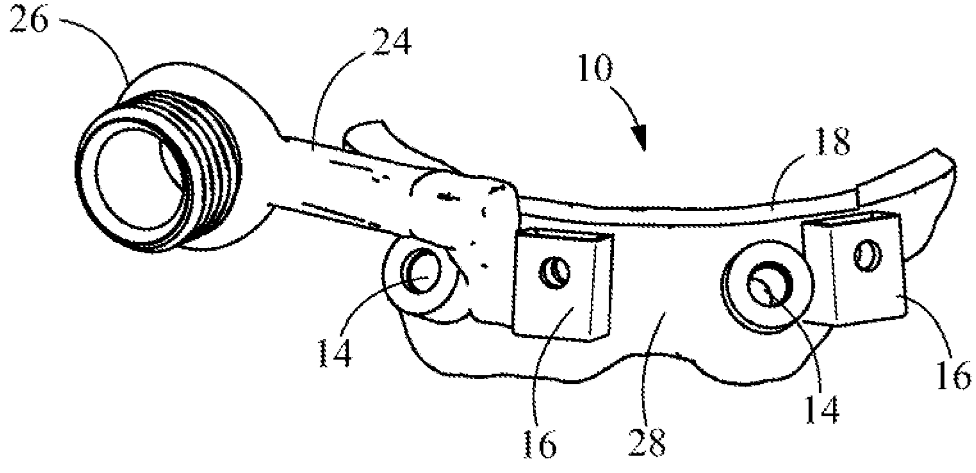
FIG. 1 is a front view of an exemplary tracker arm mount of the present invention.
Figure 1A:
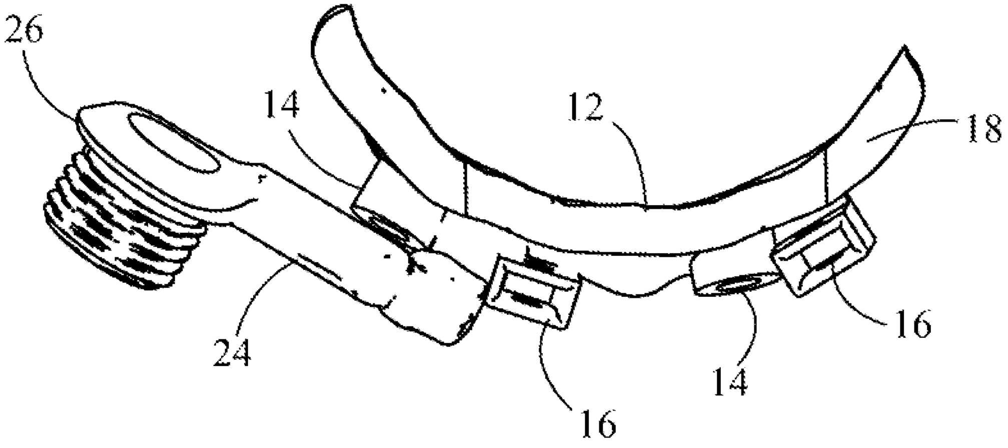
FIG. 1A is a top view of the tracker arm mount of FIG. 1.
Figures 11, 12:
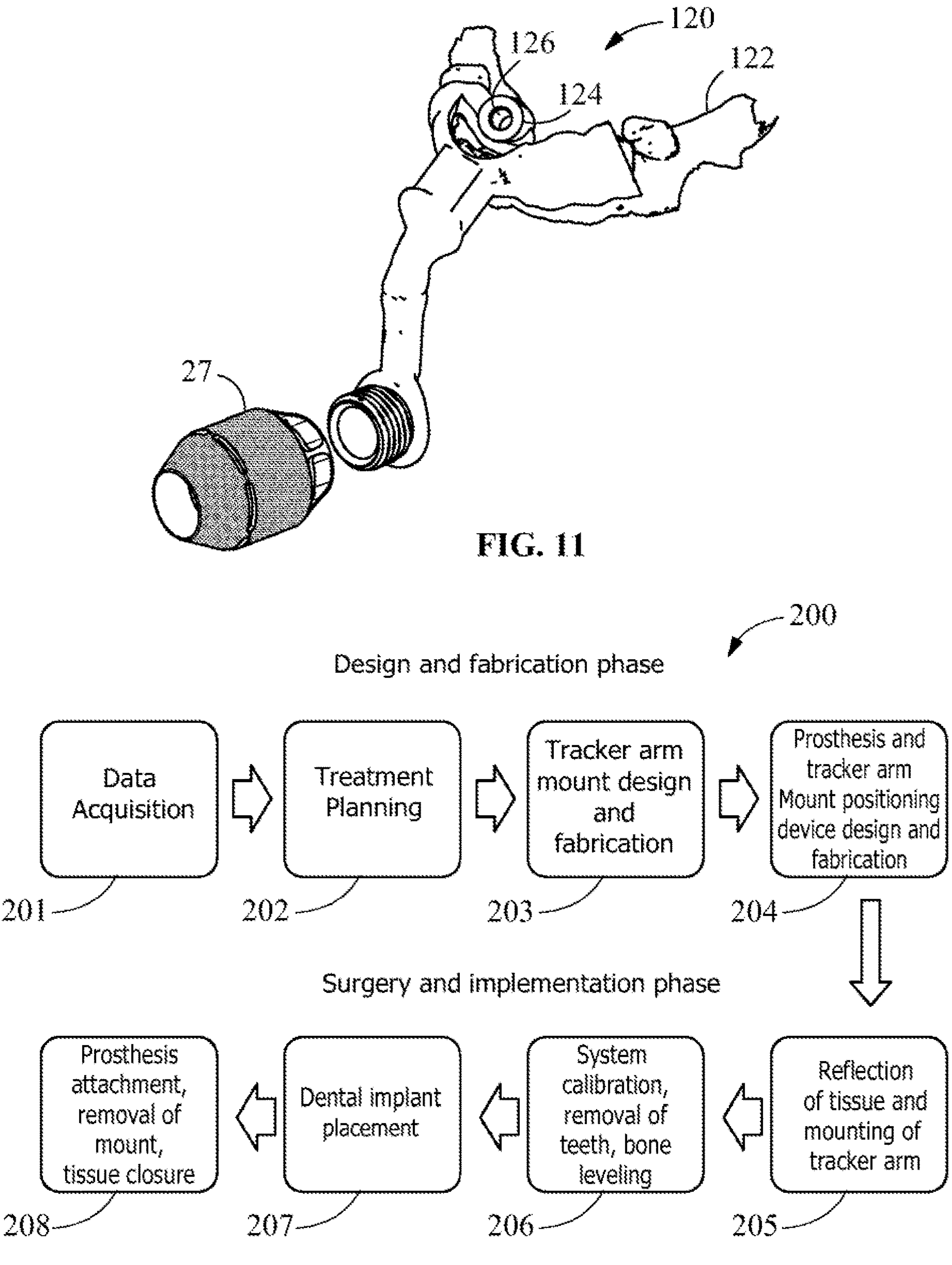
FIG. 11 is a tooth and soft tissue born tracker arm mount.
FIG. 12 is a workflow showing the steps of the workflow for dynamic navigation with the tracker arm mount.

Referring next to FIGS. 1 and 1A, a tracker arm mount 10 includes a threaded portion 26 attached by a connecting arm 24 to a body 28. Receiving slots 16 on body 28 are arranged to receive tabs 22 (FIG. 2) Apertures 14 are provided for receiving attachment devices or fasteners 52. A top surface 18 of body 28 may be used as a reference for bone leveling as described below. The inner surface 12 is designed and fabricated to closely contour the outer surface, or buccal, contour of the patient's jaw bone. Attachment apertures 14 are planned in a manner to avoid vital structures and may optionally be configured to accept reinforcement collars (not shown). Fasteners are inserted through the attachment apertures 14 to temporarily fixate the mount 10 to the patient's jaw bone as described in greater detail below. Slots 16 accept corresponding tabs 22 from a dental device, e.g., an occlusal positioning device 20 (FIG. 2), interim dental prosthesis 30 (FIG. 3), or any other dental device or component that may be added. The top surface 18 could be digitally planned in a manner to be used as a reference for bone leveling. The arm 24 connects the body 28 of tracker arm mount 10 to the threaded portion 26 to accept an optical tracking device or bulb 27 (FIG. 11)

Figure 2:
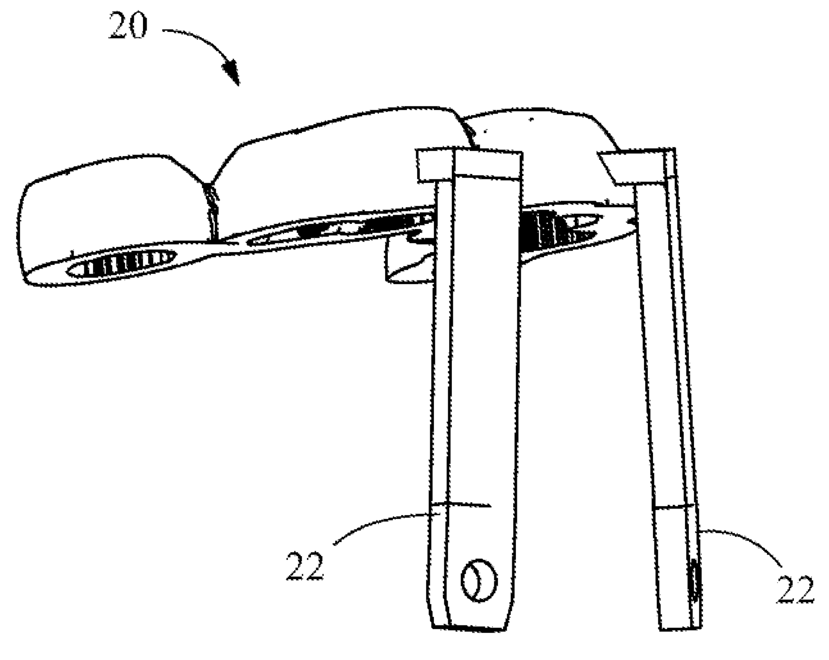
FIG. 2 is a right side perspective view of an occlusion positioning device.
Figure 2A:
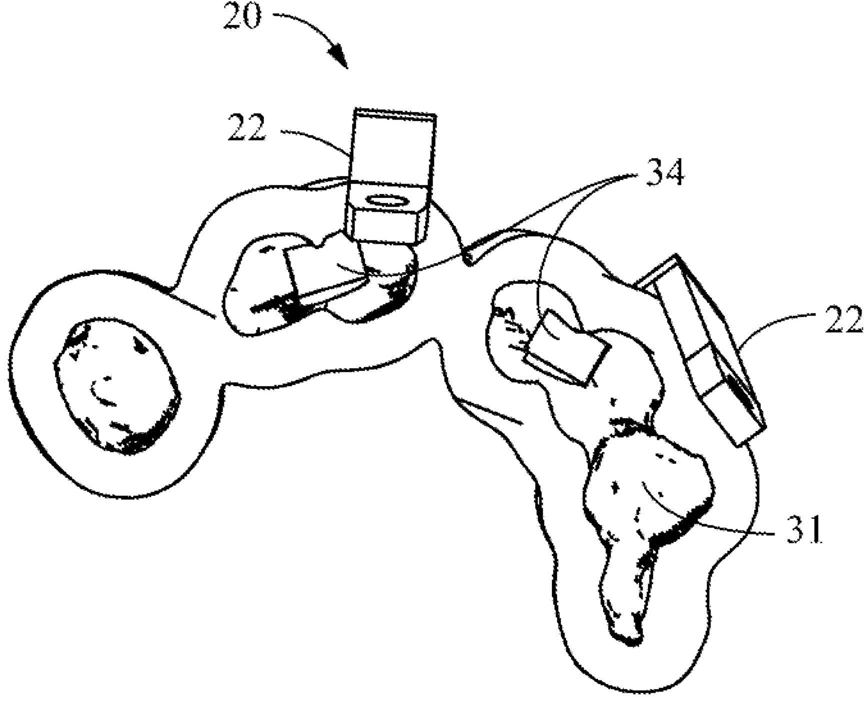
FIG. 2A is a bottom view of the occlusion positioning device of FIG. 2.

Referring next to FIGS. 2 and 2A an occlusal positioning device 20 includes a prosthesis 30 having negative tooth impressions with verification window apertures 34. Tabs 22 connected to the prosthesis 30 extend outward, generally in a perpendicular plane for connection to slots 16 on tracker arm body 28. The occlusal positioning device 20 is designed based of patient imaging records to have an undersurface 31 that closely contours the top surface of the patient's teeth 32.

Verification window apertures 34 are placed to ensure proper seating of the occlusal positioning device 20. Tabs 22 are designed to be inserted into the slots 16 of the tracker arm mount.

Figure 3:
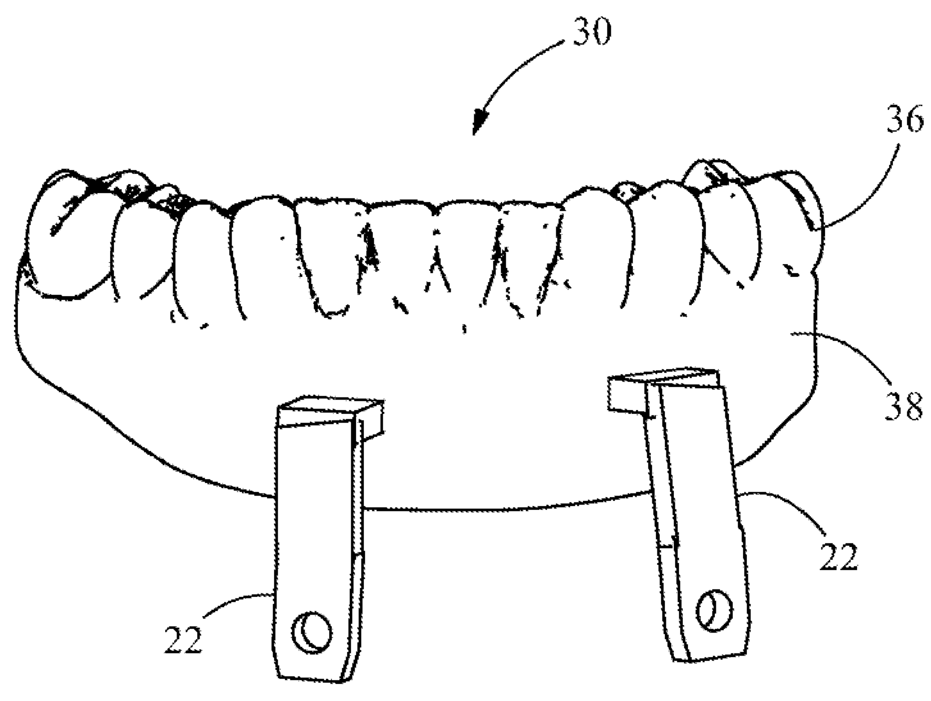
FIG. 3 shows a front view of an interim dental prosthesis.
Figure 4:
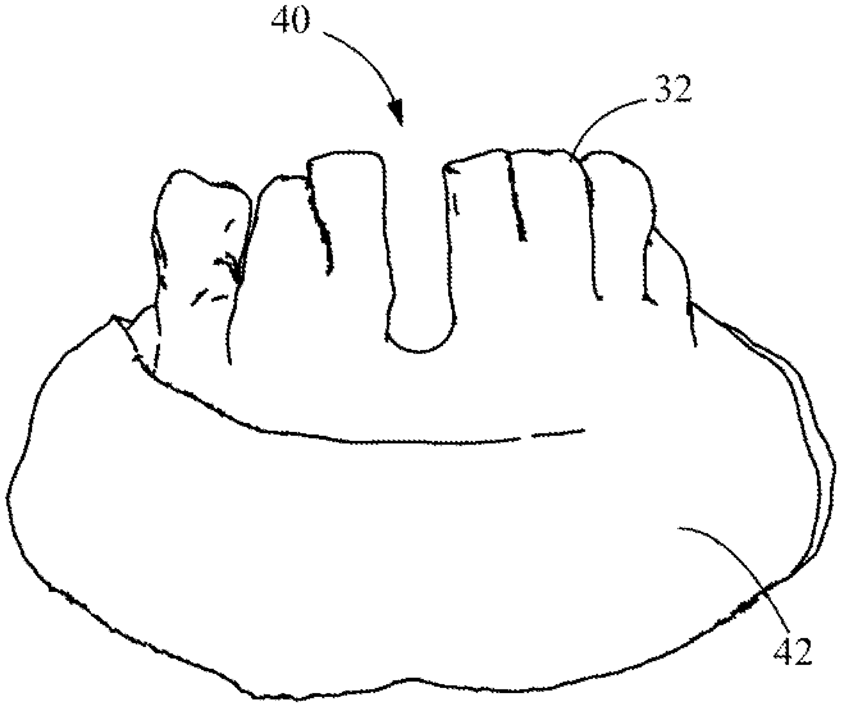
FIG. 4 is an image of a jawbone.

Referring next to FIGS. 3 and 4, prosthesis 30 is shown with a tooth portion 36 and gingival portion 38 on an interim prosthesis 30. An actual dentition 40 of a patient for removal is shown with a malocclusion and in this example, a space for a missing tooth, along with the patient's jawbone surface 42. The interim dental prosthesis 30 has a tooth portion 36 and gingival portion 38 with corresponding tabs 22 which insert into the slots 16 of the tracker arm mount. The interim dental prosthesis 30 is designed based of patient imaging records.

Figure 5:
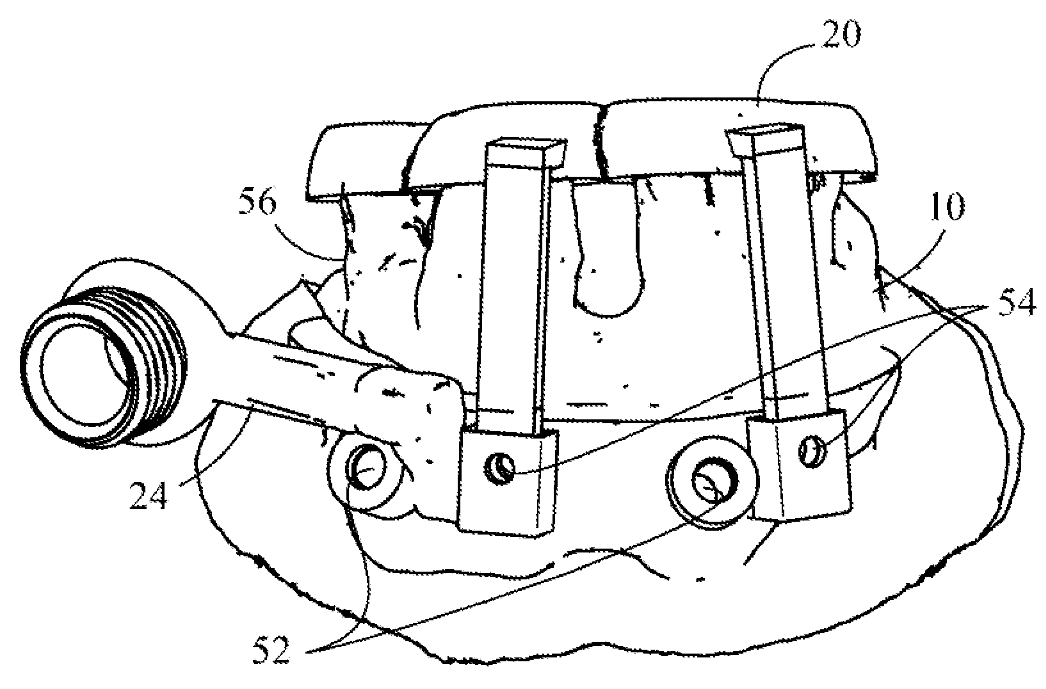
FIG. 5 is an assembled view of the tracker arm mount attached to the occlusal positioning device disposed on the jawbone.
Figure 6:
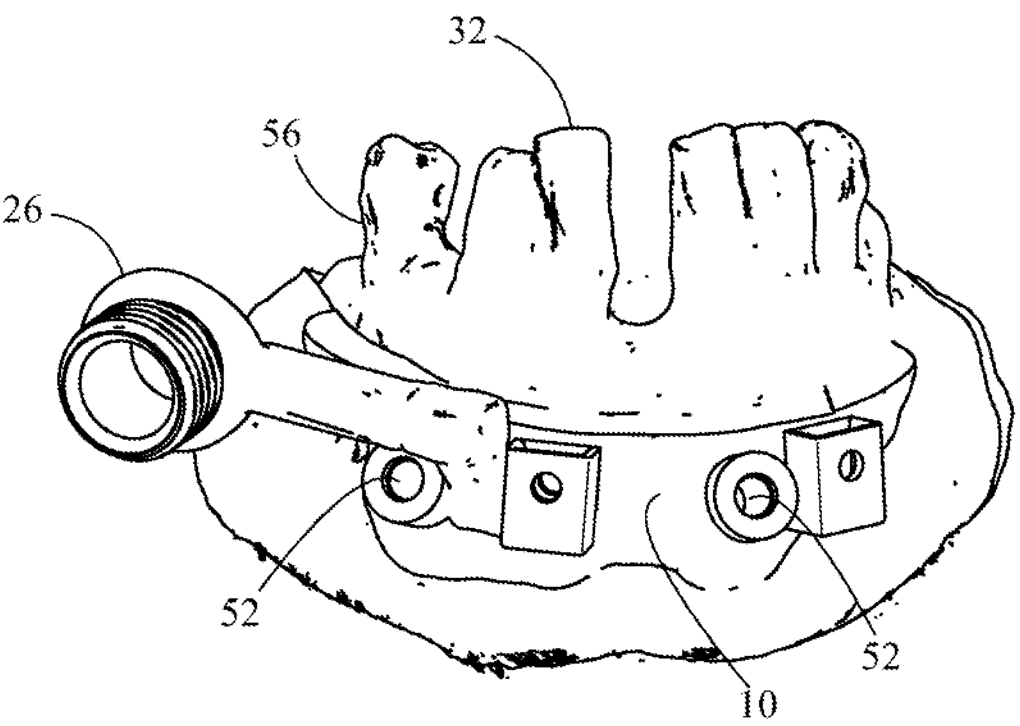
FIG. 6 is a tracker arm mount affixed to the jawbone.

A summary of a typical use is described as below:

Referring next to FIG. 5 an assembled view of the tracker arm mount 10 attached to the occlusal positioning device 20 disposed on the jawbone is shown. FIG. 6 shows a detail of the tracker arm mount affixed to the jawbone. 56 During surgery, the patient's buccal surface 42 of the jawbone 56 is visualized. The occlusal positioning device 20 tabs 22 may be inserted into the slots 16 of the tracker arm mount 10 and temporarily fixated with pins 54. The joined device is seated onto the patient's teeth 32 and verified to be in correct position through the verification window apertures 34. Fasteners 52 are placed through the attachment apertures 14 to fixate the tracker arm mount 10 to the outer surface of the jaw bone 42 for the length of the surgery. The pins 54 are removed to allow for the removal of the occlusal positioning device 20. The optical tracker bulb 27 (see, e.g., FIG. 11) is secured to the threaded portion 26 of the tracker arm mount 10. The teeth 32 are removed with surgical instruments (not shown) and the bone above the level of the tracker arm mount 56 is removed with surgical instruments (not shown). Dental implant surgery is performed in the area 70 of the reduced bone 50 and attached tracker arm mount 10 collectively seen in FIG. 7.

Once dental implant surgery is performed, an interim dental prosthesis 30 may be stacked and pinned 54 to the tracker arm mount slots 16. A "pick up" whereby dental implant components can be luted onto the interim dental prosthesis 30 can occur which allows the interim dental prosthesis to be secured to the inserted dental implants in a retrievable type fashion.

Figure 8:
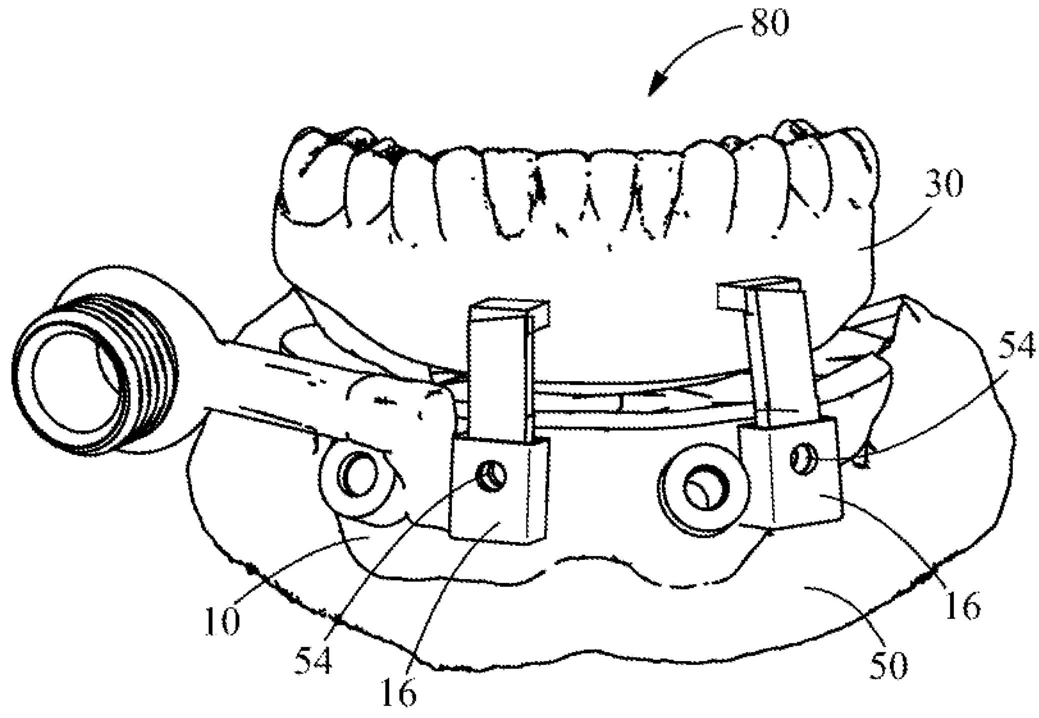
FIG. 8 shows a prosthesis attached to the tracker arm mount.

The fasteners 52 are removable to allow for removal of the tracker arm mount 10 and the post-surgical area 80 is closed in a standard fashion. A prosthesis 30 is attached to the tracker arm mount 10, as shown in FIG. 8.

Figure 9:
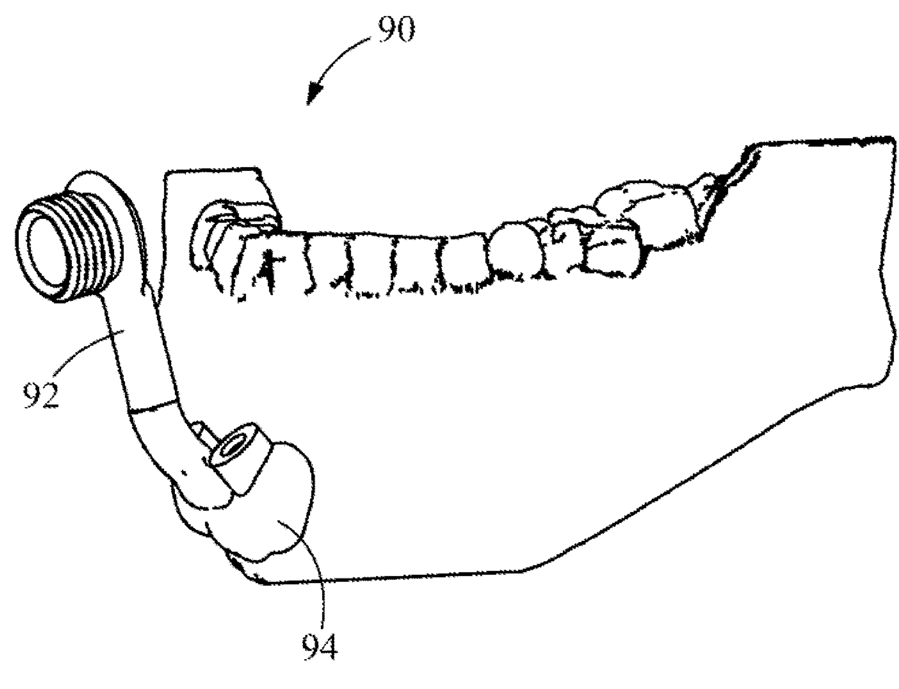
FIG. 9 is an alternate arrangement with a tracker arm that does not incorporate a top surface used as a bone leveler.
Figure 10:
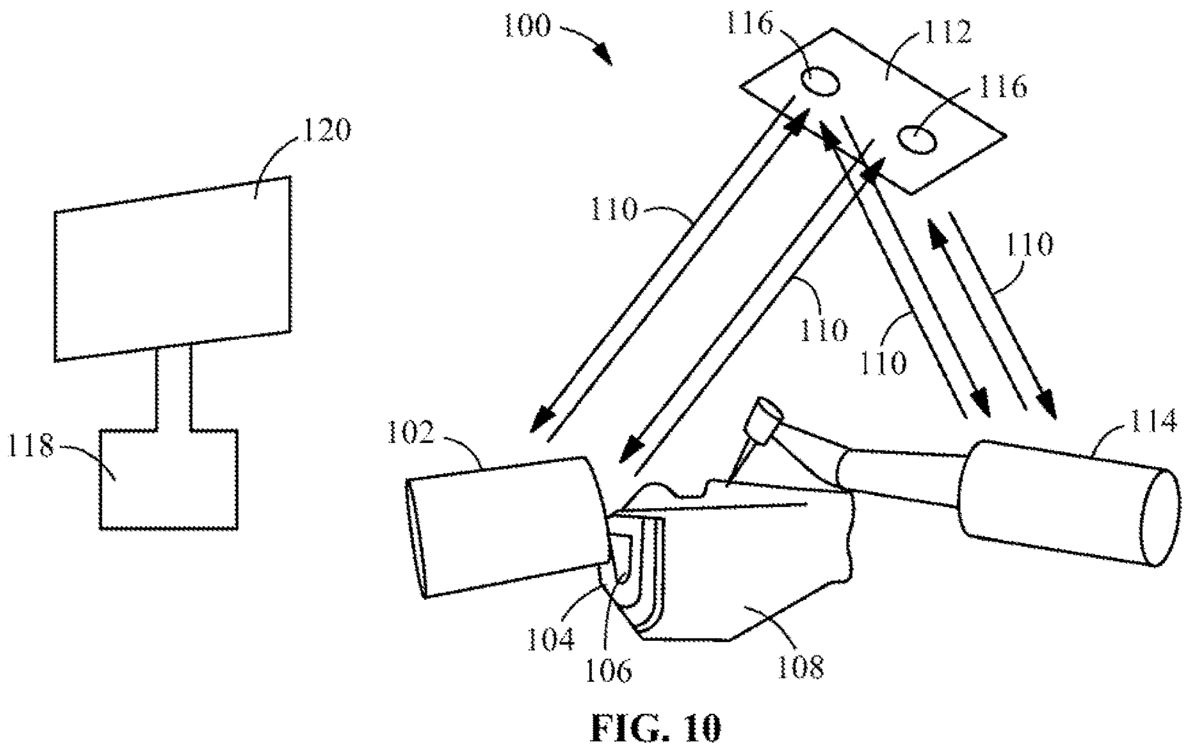
FIG. 10 is an exemplary configuration for a dynamic navigation system.

Referring next to FIG. 9 shows an alternate embodiment of a tracker arm mount 90 that does not incorporate a top surface used as a bone leveler. The tracker arm mount 90 may be used in a manner that does not incorporate a top surface to be used as a bone leveler nor without attachment apertures for other associated fixtures 92. It is designed to contour the patient's bone in planted area 94.

Referring to FIG. 11, a tooth and soft tissue born tracker arm mount 120 is designed from a patient's intra oral scan, or digital tooth impression 122. A guide tube 124 that accepts a corresponding fixation screw 126 is planned in manner as to provide adequate anchorage into the underlying jaw bone.

Referring next to FIG. 12 a flow diagram of an exemplary method and workflow for surgery using the tracker arm mount 10 of the present invention is shown. The invention and method describes an example of a patient specific tracker arm mount use for a dental full arch rehabilitation surgery.

The method 200 begins at step 201 with data acquisition. Data associated with the patient includes pertinent photos, measurements, digital impressions, and 3D x-rays (CBCT) which are taken of the patient prior to surgery. Next, the method proceeds at step 202 to perform treatment planning. The patient data acquired in step 201 is uploaded into appropriate CAD/CAM software to design a prosthesis, i.e., a new set of teeth. After the teeth are designed, dental implant treatment planning software is used to virtually place the dental implants to ensure their position into the adequate amounts of bone and in a manner to support the new teeth in an esthetic, hygienic, and structural manner.

Next, at step 203 the tracker arm mount and foundation guide are designed. Front, rear, top, bottom, left side profile, and right-side profile views of an exemplary design are shown in FIGS. 1 and 1A. From step 203, the method proceeds at step 204 to designing and fabricating the prosthesis and fabricating the tracker arm mount positioning device as described above with respect to FIGS. 2 and 3 FIG. 2 shows front, rear, top, bottom, left side profile, and right side profile views of the design prosthesis. FIG. 3 shows front, rear, top, bottom, left side profile, and right-side profile views of the tracker arm mount positioning device.

Next, the method proceeds at step 205 to performing reflection of the gum tissue and temporary mounting of the tracker arm mount. FIG. 4 is an example of the underlying jaw bone and corresponding teeth to be removed. FIG. 5 shows how the tracker arm mount positioning device fits securely onto the teeth to accurately position the tracker arm mount. FIG. 6 shows the tracker arm mount and jaw bone with the positioning device removed.

Figure 7:
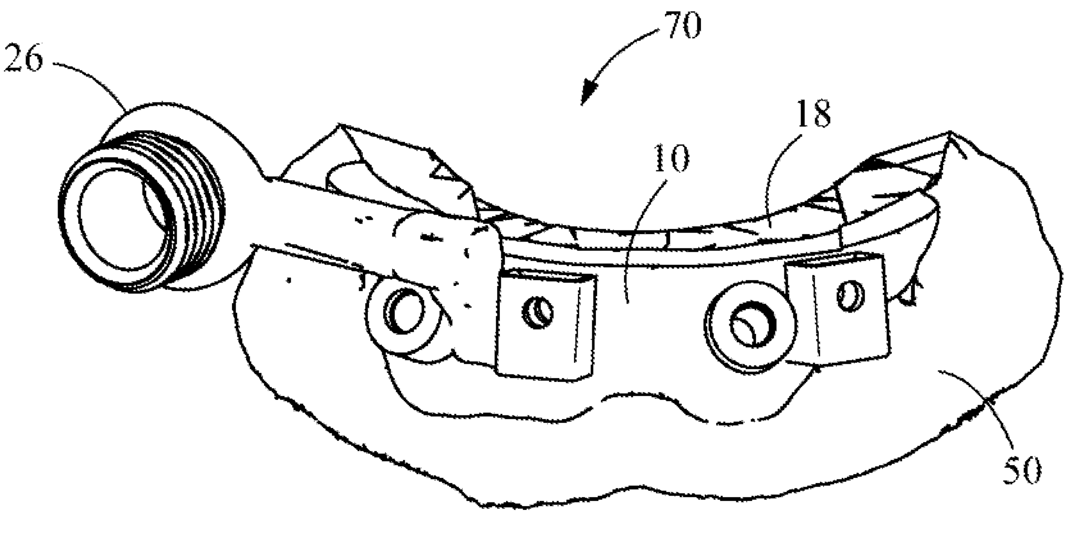
FIG. 7 shows the teeth removed and the jaw bone planed flush with the tracker arm mount.

At step 206 an optical tracker bulb is attached to the tracker arm mount 10, 90, and the dynamic navigation system is calibrated. The surgeon removes the teeth and planes the bone to the top 18 or the foundation guide (FIG. 7).

Next at step 207 the surgeon uses the dynamic navigation system to place the dental implants (not shown.) Implant attachments, temporary cylinders, are screwed into the tops of the dental implants in the manner which is well-known to persons of skill in the art.

Finally, at step 208 the prosthesis is attached to the tracker arm mount and is luted to the temporary cylinders with dental light cure composite material. Once set, the cylinders are unscrewed and the prosthesis and connected temporary cylinders may be removed from the mouth. The attachments are removed, and the prosthesis is smoothed, polished. The tracker arm mount 10, 90 is then removed. The prosthesis is reinserted, screwed into the dental implants. The gum tissue is repositioned and sutured closed.

In an exemplary embodiment the steps for designing the described tracker arm mount 10, connecting arm 24 and various components is described below.

First, patient data such as CBCT, digital impressions of the maxillary and mandibular teeth, important facial and intraoral measurements, and patient photos are acquired.

Next, a virtual wax up of the desired new teeth and gums is created in dental CAD/CAM software. in one embodiment the software may be, exocadDentalCAD by Evident Labs of Vancouver Canada, or similar software. The design is based on the existing occlusion of the maxillary and mandibular teeth, important measurements, and intra and extra oral patient photos. The virtual wax up is saved in a Standard Tessellation Language (STL) format.

Then a dental implant virtual treatment plan is created in dental implant treatment planning software. A non-limiting example of the planning software used is X-Guide treatment planning software by Nobel Biocare. The patient CBCT is uploaded into the dynamic navigation treatment planning software. The virtual wax up, in stl file format, is aligned, or meshed onto the patients CBCT. The dental implants are placed in a manner to provide optimal support of the prosthesis, allow anchorage in bone of sufficient quantity and quality, and be clear of any and all vital structures. Dental implants are available in varying widths and lengths to allow the designer and surgeon flexibility in implant placement.

Next, the position of the CBCT, planned implants, and designed prosthesis are exported as one stl file.

A case is created in a dental implant treatment planning software which allows for design of static guides. Examples of such software include: exoplan, by exocad GmbH, Real-Guide by 3DIEMME Company, and 360DPS. by 360Imaging The tracker arm mount is designed on based on such variables as implant positioning and planned bone leveling. An occlusal positioning jig is designed based on the patient's existing teeth position and planned tracker arm mount. A soft tissue format of the patient's CBCT is generated allowing visualization of the patient's extraoral facial characteristics. The tracker arm mount and CBCT soft tissue format are saved and exported as stl file formats.

A standard CAD software is then opened and the soft tissue format and tracker arm mount are imported. One example of suitable CAD software is Meshmixer. Using the soft tissue surface as a reference, a previously designed tracker array and its corresponding attachment threads having the same dimensions as the actual patient tracker array, is virtually placed in a manner as to provide the optimal direct view with the overhead stereotactic cameras during the actual dental implant surgery. This position is ideally selected with input from the performing surgeon. The tracker array and threads are saved as separate stl files.

Next, a case is created in the exocad PartialCAD and the tracker arm mount, soft tissue format, tracker array, and tacker array threads, files are imported. Other software which may be used include any organic type CAD application such as Geomagic. The arm is designed connecting the tracker arm mount to the threads which accept the tracker array.

The previously created Meshmixer case is then opened and the completed foundation mount, occlusal positing jig, and virtual wax up are imported to the previously saved objects. Struts and attachments are designed allowing the occlusal positioning jig and virtual wax up to be secured to the underlying foundation mount with pins. The completed foundation mount, occlusal positioning jig, and virtual are exported as individual stl file.

Finally, the objects described as above are fabricated with materials per their intended use in either an additive or subtractive type manner."

While the exemplary embodiments illustrated in the figures and described herein are presently preferred, it should be understood that these embodiments are offered by way of example only. Accordingly, the present application is not limited to a particular embodiment, but extends to various modifications that nevertheless fall within the scope of the appended claims. The order or sequence of any processes or method steps may be varied or re-sequenced according to alternative embodiments.

The present application contemplates methods, systems and program products on any machine-readable media for accomplishing its operations. The embodiments of the present application may be implemented using an existing computer processors, or by a special purpose computer processor for an appropriate system, incorporated for this or another purpose or by a hardwired system.

It is important to note that the construction and arrangement of the dynamic navigation tracker arm mount apparatus and method as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present application. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the exemplary embodiments without departing from the scope of the present application.

As noted above, embodiments within the scope of the present application include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

It should be noted that although the figures herein may show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the application. Likewise, software implementations could be accomplished with standard programming techniques with rule based logic and other logic to accomplish the various connection steps, processing steps, comparison steps and decision steps.

The invention claimed is:

1. An oral fixture for use in a dynamic navigation system for oral and maxillofacial surgery, comprising:

a tracker arm, a tracker arm mount, and at least one fastener;

the tracker arm comprising a threaded portion attached by a connecting arm to the tracker arm mount, the threaded portion being configured to receive to an optical tracking device for dynamic navigation;

the tracker arm mount having a body comprising a top surface and an inner surface designed from computed tomography (CT) corresponding with an outer surface contour of the buccal surface of a jawbone specific to a patient, a plurality of receiving slots configured to receive tabs from dental device components, and a plurality of apertures positioned to receive fasteners while avoiding vital anatomical structures and planned implant locations, wherein the body is configured to fit on the outer surface contour of the jawbone;

at least one aperture of the plurality of apertures adapted to receive a fastener for attachment of the oral fixture to the jawbone, wherein the tracker arm is adapted to be attached to the jawbone via the tracker arm mount and fastener;

wherein the aperture adapted to receive the fastener for attachment of the oral fixture to the jawbone is monolithically formed with the tracker arm and tracker arm mount;

wherein the fastener is capable of engaging the full thickness of the jawbone for secure temporary fixation of the tracker arm and tracker arm mount during oral and maxillofacial surgery.

2. The oral fixture of claim 1, further comprising:

a dental device comprising a plurality of tabs, the tabs corresponding to the receiving slots in the body for connecting the dental device to the body tracker arm mount.

3. The oral fixture of claim 2, wherein the dental device comprises an occlusal positioning device comprising a prosthesis having negative tooth impressions; the tabs extending outward, for connection to the receiving slots;

the occlusal positioning device having an undersurface; the undersurface comprising contours corresponding with a top surface of a patient's teeth.

4. The oral fixture of claim 3, wherein the occlusal positioning device further comprises a plurality of verification window apertures; the verification window apertures disposed in the occlusal positioning device to ensure proper seating of the occlusal positioning device on the patient's teeth.

5. The oral fixture of claim 4, wherein the tabs are insertable into the corresponding receiving slots via a pin to join the body of the tracker arm mount and the dental device and to seat the dental device onto the patient's teeth; the patient's teeth being partially viewable through the verification window apertures to confirm a predetermined position.

6. The oral fixture of claim 5, further comprising an ultraviolet light source, a patient tracker, an instrument tracker, at least one stereotactic camera, and a dynamic navigation unit;

wherein the oral fixture is fixated to the jawbone and the patient tracker is secured onto the tracker arm; the ultraviolet light source is reflected off of the patient tracker and the instrument tracker; the patient tracker and the instrument tracker in data communication with the at least one stereotactic cameras to generate camera data; the stereotactic camera data configured to transmit the camera data to a dynamic navigation unit.

7. The oral fixture of claim 6, further comprising a monitor in data communication with a processor of the dynamic navigation system; the monitor configured to display the camera data.

8. The oral fixture of claim 6, wherein the tracker arm mount is based on one of an intra oral scan or a digital tooth impression; and having a guide tube for accepting a fixation screw to provide anchorage into the underlying jawbone.

9. The oral fixture of claim 1, wherein the fastener is a screw capable of engaging the full thickness of a jawbone.

10. The oral fixture of claim 1, wherein the top surface of the body of the tracker arm mount is configured as a reference for jawbone leveling.

11. An oral fixture for oral and maxillofacial surgery, comprising:

a tracker arm and a tracker arm mount;

the tracker arm comprising a threaded portion for receiving an optical tracking device for dynamic navigation guidance;

the tracker arm mount having at least one aperture for receiving a fastener adapted to be attached to the buccal surface of a jawbone, wherein the is directly affixed to the jawbone via the tracker arm mount with the fastener on the end opposite the threaded portion;

wherein the aperture is monolithically formed with the tracker arm and tracker arm mount;

wherein the fastener is capable of engaging the full thickness of the jawbone for secure temporary attachment during surgery;

the tracker arm mount having a body designed from computed tomography (CT) customized to fit said jawbone;

the tracker arm mount having at least one receiving slot configured to receive an occlusal positioning device disposed on the jawbone.

12. The oral fixture of claim 11, wherein the body of the tracker arm mount is configured as a reference for jawbone leveling.

* * * * *